(12) United States Patent
Ley et al.

(10) Patent No.: US 8,778,987 B2
(45) Date of Patent: Jul. 15, 2014

(54) USE OF 4-HYDROXYCHALCONE DERIVATIVES FOR MASKING AN UNPLEASANT TASTE

(75) Inventors: Jakob Ley, Holzminden (DE); Susanne Paetz, Hoexter (DE); Thomas Riess, Holzminden (DE); Gerhard Krammer, Holzminden (DE)

(73) Assignee: Symrise AG, Holzminden (DE)

( * ) Notice: Subject to any disclaimer, the term of this patent is extended or adjusted under 35 U.S.C. 154(b) by 625 days.

(21) Appl. No.: 12/046,978

(22) Filed: Mar. 12, 2008

(65) Prior Publication Data

US 2008/0227867 A1 Sep. 18, 2008

(51) Int. Cl.
A23F 3/40 (2006.01)
A23L 1/226 (2006.01)
A61K 47/22 (2006.01)
A61K 31/12 (2006.01)

(52) U.S. Cl.
USPC ............... 514/456; 426/3; 426/538; 426/548; 426/590; 426/650; 562/464; 514/698

(58) Field of Classification Search
USPC .............. 514/456, 698; 426/3, 538, 548, 590, 426/650; 562/464
See application file for complete search history.

(56) References Cited

U.S. PATENT DOCUMENTS

| | | | |
|---|---|---|---|
| 3,932,678 A * | 1/1976 | Rizzi ............................. | 426/548 |
| 3,976,790 A | 8/1976 | Crosby et al. | |
| 4,154,862 A | 5/1979 | Guadagni et al. | |
| 5,045,336 A | 9/1991 | Lindley et al. | |
| 5,580,545 A | 12/1996 | Washino et al. | |
| 5,637,618 A | 6/1997 | Kurtz et al. | |
| 5,643,941 A | 7/1997 | Kurtz et al. | |
| 2002/0177576 A1 | 11/2002 | McGregor et al. | |
| 2002/0188019 A1 * | 12/2002 | Ley et al. ...................... | 514/456 |
| 2005/0234132 A1 | 10/2005 | Gatfield et al. | |
| 2006/0286237 A1 | 12/2006 | Reiss et al. | |
| 2006/0286276 A1 | 12/2006 | Salemme et al. | |

FOREIGN PATENT DOCUMENTS

| | | |
|---|---|---|
| EP | 635218 A1 | 1/1995 |
| EP | 1258200 A2 | 11/2002 |
| GB | 2380936 A1 | 4/2003 |
| JP | 10276712 | 10/1998 |
| WO | WO-00/21390 A1 | 4/2000 |
| WO | WO-2004/000787 A2 | 12/2003 |
| WO | WO-2004/043960 A1 | 5/2004 |
| WO | WO-2004/078302 A1 | 9/2004 |
| WO | WO-2005/096841 A1 | 10/2005 |
| WO | WO-2006/024587 A1 | 3/2006 |
| WO | WO-2006/058893 A2 | 6/2006 |
| WO | WO-2006/106023 A1 | 10/2006 |
| WO | WO-2007/003527 A1 | 1/2007 |
| WO | WO-2007/014879 A1 | 2/2007 |
| WO | WO-2007/045566 A1 | 4/2007 |
| WO | WO-2007/107596 A1 | 9/2007 |

OTHER PUBLICATIONS

Jez et al, the Journal of Biological Chemistry, vol. 277, No. 2, 2002, pp: 1361-1369.*

Yamato M. et al., "Chemical structure and sweet taste of isocoumarins and related compounds. Synthesis of 5-hydroxyflavanones and related dihydrochalcones," Chemical and Pharmaceutical Bulletin, 1977, JP, Bd. 25, Nr. 6, 1977, Seiten, 1484-1486, XP002489894, ISSN: 0009-2363, *Seite 1485; Tabelle I*.

Yamato M. et al., "Chemical structure and sweet taste of isocoumarins and related compounds. X. Syntheses of sweet 5-hydroxyflavanones and related dihydrochalcones," Chemical and Pharmaceutical Bulletin, 1978, JP, Bd. 26, Nr. 8, 1978, Seiten 2321-2327, XP002489895, ISSN: 0009-2363, *Seite 2324; Tabelle I*, *Seite 2325; Abbildung 2*.

Dubois G. E. et al., "Dihydrochalcone Sweeteners. A study of the Atypical Temporal Phenomena," Journal of Medicinal Chemistry, USAmerican Chemical Society., Washington, Bd. 24, Jan. 1, 1981, Seiten 408-428, XP002345673, ISSN: 0022-2623, *Seite 414; Tabelle I*.

* cited by examiner

*Primary Examiner* — Savitha Rao
(74) *Attorney, Agent, or Firm* — Novak Druce Connolly Bove + Quigg LLP

(57) ABSTRACT

The use is described of the 4-hydroxychalcone derivatives of the formula (I)

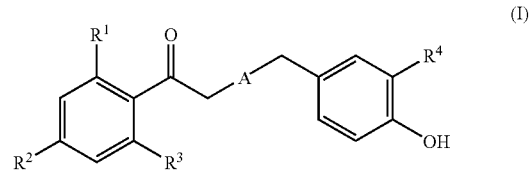

wherein
A may represent a single or double bond,
$R^1$, $R^2$ and $R^3$, mutually independently, may in each case mean H, OH or (preferably $C_1$-$C_4$) alkoxy, providing that at least one of the residues $R^1$ to $R^3$ means OH,
and
$R^4$ means H, OH or (preferably $C_1$-$C_4$) alkoxy,
and/or
(ii) the salts thereof
and
(iii) mixtures thereof
to mask or reduce the unpleasant taste impression of an unpleasant tasting substance, as are corresponding methods and preparations.

13 Claims, No Drawings

USE OF 4-HYDROXYCHALCONE DERIVATIVES FOR MASKING AN UNPLEASANT TASTE

The invention relates to the use of specific 4-hydroxychalcone derivatives, the salts thereof and mixtures thereof for masking or diminishing unpleasant taste impressions, in particular bitter, astringent and/or metallic taste impressions. The invention additionally relates to specific preparations, which contain an effective content of the stated 4-hydroxychalcone derivatives, the salts thereof or mixtures thereof.

Foodstuffs or products consumed for pleasure frequently contain various bitter substances, which on the one hand are desirable and characteristic in moderation (for example caffeine in tea or coffee, quinine in so-called Bitter Lemon beverages, hop extracts in beer), but on the other hand may severely reduce value (for example flavonoid glycosides and limonoids in citrus juices, the bitter aftertaste left by many artificial sweeteners such as aspartame or saccharin, hydrophobic amino acids and/or peptides in cheese).

To reduce the natural content of bitter substances, subsequent treatment is therefore often necessary, for example extractive treatment such as decaffeination of tea or coffee, or enzymatic treatment, for example treatment of orange juice with a glycosidase to destroy the bitter naringin or the use of specific peptidases when ripening cheese. This treatment is a strain on the product, produces waste substances and also gives rise for example to solvent residues and other residues (enzymes) in the products.

It is therefore desirable to find substances which can effectively suppress or at least reduce unpleasant taste impressions, in particular bitter, astringent and/or metallic taste impressions.

It is particularly important to suppress the bitter taste of many pharmaceutical active ingredients, since such suppression may markedly increase the readiness of the patient, in particular in the case of patients sensitive to bitterness such as children, to take the active-ingredient containing preparation orally. Many pharmaceutical active ingredients, for example aspirin, salicin, paracetamol, ambroxol or quinine, to mention just a very small selection for clarification, have a pronounced bitter, astringent and/or metallic taste and/or aftertaste.

The increased use of potassium salts in the place of sodium salts constitutes an increasingly important masking problem. In particular, sodium chloride is now frequently replaced in spicy applications at least partially by potassium chloride, which is indeed used as a salty tasting salt but also causes a number of additional, unpleasant taste impressions and in particular is described as bitter and metallic tasting.

Although a number of substances are known which can partially suppress the bitter taste, many of them are severely limited in application.

In U.S. Pat. No. 5,637,618 a bitter taste, in particular the bitter taste of potassium salts, is reduced by means of lactisole [2O-(4-methoxyphenyl)lactic acid]. However, this inhibitor simultaneously severely inhibits the sweet taste impression (cf. U.S. Pat. No. 5,045,336), which severely limits applicability.

2,4-Dihydroxybenzoic acid potassium salt is described in U.S. Pat. No. 5,643,941 (table, column 3, line 18) as an agent for masking the bitter taste of potassium chloride or potassium salts but cannot for example suppress the taste of caffeine.

According to GB 2,380,936, suppression of the taste of bitter pharmaceuticals may be achieved using ginger extracts. However, ginger extracts are not suitable for many applications, since they produce a strong aroma impression and/or their frequently perceived spiciness is troublesome.

In U.S. Pat. No. 5,580,545, although taste-modifying properties are described for a number of flavones (2-phenylchrom-2-en-4-one), no bitterness-reducing or -suppressing effect was disclosed.

US 2002 177,576 describes the suppression of a bitter taste by nucleotides, for example cytidine 5'-monophosphate (CMP). However, these highly polar compounds, which can therefore only be used in highly polar solvents, can only be used to a very limited degree in many fatty foods. In addition, the availability of such substances is severely limited due to the complex chemical synthesis thereof.

US 2006/286276 describes mixtures of nucleotides, for example adenosine 5-monophosphate (AMP) with the amino acid taurine, which in reduced common salt applications, which simultaneously have an elevated content of potassium chloride, may at least partially reduce the bitter and metallic taste of the potassium salts.

US 2002/0188019 describes hydroxyflavanones as effective bitterness masking agents, which are difficult to obtain synthetically and are not available in large quantities at a reasonable price.

The sodium salts sodium chloride, sodium citrate, sodium acetate and sodium lactate display a bitterness-masking effect relative to many bitter substances (for example *Nature*, 1997, vol. 387, p. 563); however, the consumption of relatively large quantities of sodium ions may lead, for example, to cardiac/circulatory disorders. In addition, a significant bitterness-masking effect only disadvantageously comes about at relatively high sodium concentrations (from approx. 0.1 M), which corresponds for example to a generally unacceptable elevated content of approx. 0.6 wt. % NaCl in the final application (cf. R. S. J. Keast, P. A. S. Breslin and G. K. Beauchamp, Chimia 2001, 55(5), 441-447).

WO 00121390 describes polyglutamic acid as a bitterness-masking agent; relatively elevated concentrations in the range of around 1 wt. % being required here.

A lipoprotein consisting of β-lactoglobulin and phosphatidic acid, likewise displays a bitterness-masking effect (EP A 635 218). Such polymers are difficult to characterize and standardize, however, and display a pronounced soapy off-flavor.

The flavone glycoside neodiosmin [5,7-dihydroxy-2-(4-methoxy-3-hydroxyphenyl)-7-O-neohesperidosyl-chrom-2-en-4-one] likewise exhibits a bitterness-masking action (U.S. Pat. No. 4,154,862) but is distinguished by a disaccharide residue, which makes the substance much more difficult to prepare, or isolate, and use.

WO 2005/096841 proposes γ-aminobutyric acid as a bitterness-masking agent; although this is effective, it additionally gives the preparation a slightly sour taste. WO 2006/024587 describes hydroxybenzoic acid vanillyl amides as a masking agent for a bitter taste; likewise a number of short-chain ginger dione derivatives according to WO 2007/003527 and hydroxydeoxybenzoins according to WO 2006/106023, none of which occur naturally.

The primary object of the present invention was to find substances which (a) are suitable for masking or reducing the unpleasant taste impression of substances that taste unpleasant (and preferably in particular exhibit a bitterness-masking effect against a large number of bitter substances) (b) are widely usable, (c) are readily accessible and (d) ideally occur naturally.

The stated object is achieved according to the invention by the use of
of a 4-hydroxychalcone derivative of the formula (I)

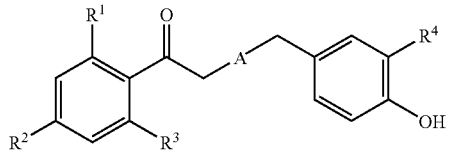

wherein
A may represent a single or double bond,
$R^1$, $R^2$ and $R^3$, mutually independently, may in each case mean H, OH or (preferably $C_1$-$C_4$) alkoxy, providing that at least one of the residues $R^1$ to $R^3$ means OH,
and $R^4$ means H, OH or (preferably $C_1$-$C_4$) alkoxy,
and/or
    a salt of such a 4-hydroxychalcone derivative of the formula (I),
    a mixture comprising or consisting of two or more different 4-hydroxychalcone derivatives of the formula (I), wherein $R^1$, $R^2$, $R^3$ and $R^4$ in each case have the above-stated meaning,
    a mixture comprising or consisting of salts of two or more different 4-hydroxychalcone derivatives of the formula (I), wherein $R^1$, $R^2$, $R^3$ and $R^4$ in each case have the above-stated meaning,
or
    a mixture comprising or consisting of
a 4-hydroxychalcone derivative of the formula (I) or two or more different 4-hydroxychalcone derivatives of the formula (I), wherein $R^1$, $R^2$, $R^3$ and $R^4$ in each case have the above-stated meaning, and
a salt of a 4-hydroxychalcone derivative of the formula (I) or two or more salts of different 4-hydroxychalcone derivatives of the formula (I), wherein $R^1$, $R^2$, $R^3$ and $R^4$ in each case have the above-stated meaning,
to modify, mask or reduce the unpleasant taste impression of an unpleasant tasting substance, in particular a bitter taste or bitter aftertaste.

Unpleasant tasting substances for the purposes of the invention are:
(a) substances which taste bitter, astringent, cardboardy, dusty, dry, floury, rancid and/or metallic and
(b) substances that have a bitter, astringent, cardboardy, dusty, dry, floury, rancid or metallic aftertaste.

The above-mentioned unpleasant tasting substances may also possess further flavor and/or odor qualities which are generally not unpleasant. As further flavor qualities which are not unpleasant for the purposes of the present invention, mention may be made, for example, of spicy, umami, sweet, salty, sour, hot, cooling, warming, burning or tingling.

Substances that taste bitter, astringent, cardboardy, dusty, dry, floury, rancid or metallic are, for example: xanthine alkaloids, xanthines (caffeine, theobromine, theophylline and methylxanthine), alkaloids (quinine, brucine, strychnine, nicotine), phenolic glycosides (e.g. salicin, arbutin), flavonoid glycosides (e.g. neohesperidin, hesperidin, naringin, quercitrin, rutin), bitter tasting chalcones or chalcone glycosides (e.g. phloridzin), hydrolyzable tannins (gallic or ellagic acid esters of carbohydrates, e.g. pentagalloylglucose), non-hydrolyzable tannins (optionally galloylated catechols or epicatechols and oligomers thereof, e.g. proanthyocyanidines or procyanidines, thearubigin), flavones (e.g. quercertin, taxifolin, myricetin), phenols such as for example salicin, polyphenols (e.g. γ-oryzanol, caffeic acid or esters thereof), terpenoid bitter substances (e.g. limonoids such as limonin or nomilin from citrus fruits, lupolones and humulones from hops, iridoids, secoiridoids), absinthin from wormwood, amarogentin from gentian, metal salts (in particular potassium, magnesium and calcium salts, potassium chloride, potassium gluconate, potassium carbonate, potassium sulfate, potassium lactate, potassium glutamate, potassium succinate, potassium malate, sodium sulfate, magnesium sulfate), pharmaceutical active ingredients (e.g. fluoroquinolone antibiotics, paracetamol, aspirin, β-lactam antibiotics, ambroxol, propylthiouracil [PROP], guaifenesin), vitamins (for example vitamin H, vitamins from the B group, such as vitamin B1, B2, B6, B12, niacin, pantothenic acid), denatonium benzoate, sucralose octaacetate, iron salts, aluminum salts, zinc salts, urea, unsaturated fatty acids, in particular unsaturated fatty acids in emulsions, bitter tasting amino acids (e.g. leucine, isoleucine, valine, tryptophan, proline, histidine, tyrosine, lysine or phenylalanine) and bitter tasting peptides (in particular peptides having an amino acid from the group leucine, isoleucine, valine, tryptophan, proline or phenylalanine at the N- or C-terminus). Preferred substances which taste bitter, astringent, cardboardy, dusty, dry, floury, rancid or metallic are caffeine, theobromine and theophylline, quinine, salicin, arbutin, neohesperidin, naringin, quercitrin, rutin, phloridzin, gallic or ellagic acid esters of carbohydrates (e.g. pentagalloylglucose), optionally galloylated catechols or epicatechols, proanthyocyanidines or procyanidines, thearubigin, quercetin, taxifolin, myricetin, γ-oryzanol, caffeic acid or esters thereof (e.g. chlorogenic acid and isomers), limonoids such as limonin or nomilin from citrus fruits, lupolones and humulones from hops, absinthin from wormwood, amarogentin from gentian, metal salts (in particular potassium, magnesium and calcium salts, potassium chloride, potassium gluconate, potassium carbonate, potassium sulfate, potassium lactate, potassium glutamate, potassium succinate, potassium malate, sodium sulfate, magnesium sulfate) and pharmaceutical active ingredients (e.g. fluoroquinolone antibiotics, paracetamol, aspirin, β-lactam antibiotics, ambroxol, propylthiouracil [PROP], guaifenesin).

Substances that have a bitter, astringent, cardboardy, chalky, dusty, dry, floury, rancid or metallic aftertaste may be aroma substances or flavorings having a not unpleasant primary flavor (for example sweet, salty, spicy, sour) and/or odor and may belong, for example, to the group comprising sweeteners, sugar substitutes or aroma substances. Examples which may be mentioned are: potassium salts (in particular potassium chloride, potassium gluconate, potassium carbonate, potassium sulfate, potassium lactate, potassium glutamate, potassium succinate, potassium malate), aspartame, neotame, superaspartame, saccharin, sucralose, tagatose, monellin, stevioside, rebaudioside, hernandulcin, thaumatin, miraculin, glycyrrhizin, glycyrrhetinic acid or derivatives thereof, cyclamate or the pharmaceutically acceptable salts of the above-mentioned compounds.

Particularly preferably, the 4-hydroxychalcone derivatives of the formula (I) according to the invention, the salts and mixtures thereof are used to modify, reduce or mask a bitter taste.

Preference is given to use of the 4-hydroxychalcone derivatives of the formula (I)

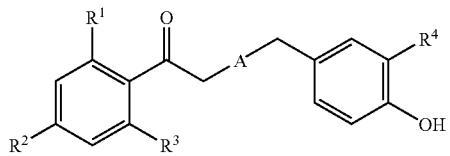

wherein
A represents a single bond,
and
$R^1$ means OH
and
$R^2$ and $R^3$, mutually independently, may mean H or OH,
and
$R^4$ means an H or methoxy,
and/or the salts and mixtures thereof as described above.

Preference is likewise given to use of the 4-hydroxychalcone derivatives of the formula (I)

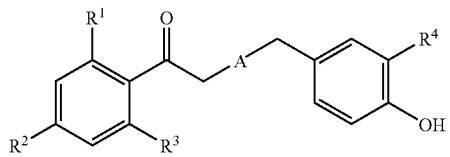

wherein
A represents a single bond,
and
$R^2$ means OH
and
$R^1$ and $R^3$ mean H,
and
$R^4$ means an H or methoxy,
and/or the salts and mixtures thereof as described above.

Particularly preferred 4-hydroxychalcone derivatives of the formula (I) are:
2',4-dihydroxydihydrochalcone or 3-(4-hydroxyphenyl)-1-(2-hydroxyphenyl)-propan-1-one (compound 1)
2',4,4'-trihydroxydihydrochalcone or 3-(4-hydroxyphenyl)-1-(2,4-dihydroxyphenyl)-propan-1-one (davidigenin, compound 2)
2',4,6'-trihydroxydihydrochalcone or 3-(4-hydroxyphenyl)-1-(2,6-dihydroxyphenyl)-propan-1-one (compound 3)
2',4,4',6'-tetrahydroxydihydrochalcone or 3-(4-hydroxyphenyl)-1-(2,4,6-trihydroxy-phenyl)propan-1-one (phloretin, compound 4)
2',4-dihydroxy-3-methoxydihydrochalcone or 3-(4-hydroxy-3-methoxyphenyl)-1-(2-hydroxyphenyl)propan-1-one (compound 5)
2',4,4'-trihydroxy-3-methoxydihydrochalcone or 3-(4-hydroxy-3-methoxyphenyl)-1-(2,4-dihydroxyphenyl)propan-1-one (compound 6)
2',4,6'-trihydroxy-3-methoxydihydrochalcone or 3-(4-hydroxy-3-methoxyphenyl)-1-(2,6-dihydroxyphenyl)propan-1-one (compound 7)
2',4,4',6'-tetrahydroxy-3-methoxydihydrochalcone or 3-(4-hydroxy-3-methoxy-phenyl)-1-(2,4,6-trihydroxyphenyl) propan-1-one (compound 8)
2',3,4,4',6'-tetrahydroxydihydrochalcone or 3-(3,4-dihydroxyphenyl)-1-(2,4,6-trihydroxyphenyl)propan-1-one (3-hydroxyphloretin, compound 9)
4,4'-dihydroxy-3-methoxy-dihydrochalcone or 3-(4-hydroxy-3-methoxyphenyl)-1-(4-hydroxyphenyl)propan-1-one (compound 10)
and the salts and mixtures thereof as described above.

Although compounds of the general formula (I), where A denotes a single bond, are already mentioned as such in WO 2007/014879, the fact that they may be used to modify, mask or reduce the unpleasant taste of an unpleasant tasting substance was not known. The compounds are only described together with hesperetin, which should be used to enhance a sweet taste.

Compounds 1 to 10 are listed again in the following Figure for the purpose of clarification (the general numbering scheme for dihydrochalcones is indicated by way of example on compound 1):

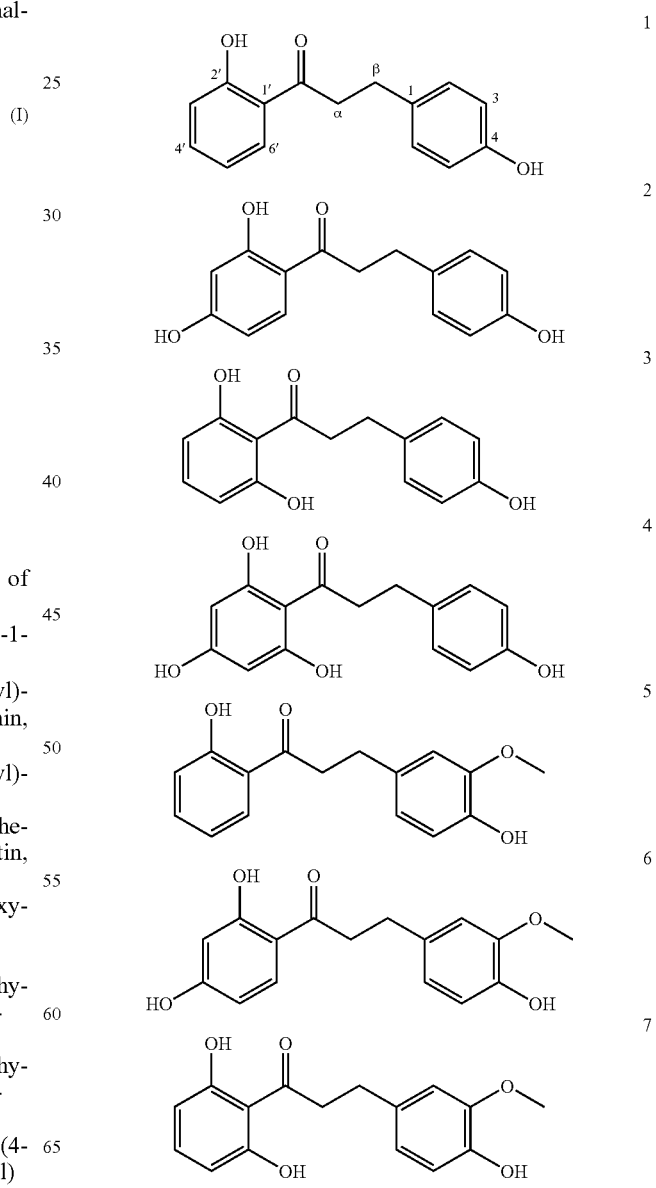

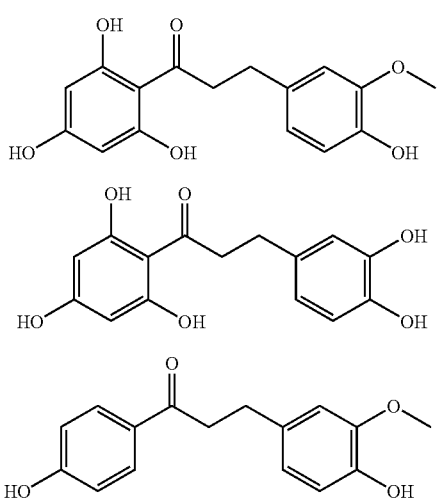

In salts of a compound of the above formula (I) to be used according to the invention (wherein the above-stated continues to apply with regard to the preferred meanings of the residues and variables) one, several or all of the hydroxy groups of compound (I) are deprotonated. A corresponding amount of countercations is then present, this preferably being selected from the group consisting of: unipositive cations of main group and subgroup I, ammonium ions, trialkylammonium ions, dipositive cations of main group and subgroup II and tripositive cations of main group and subgroup III, and mixtures thereof.

It goes without saying that the number of hydroxy groups in the underlying 4-hydroxychalcone derivatives is decisive with regard to the maximum degree of deprotonation and thus also to the amount of countercations present. If, for example, a total of two hydroxy groups are present in the underlying 4-hydroxychalcone derivatives, in the case of complete deprotonation of the hydroxy groups a dinegative anion is present, such that a corresponding number of positive charges has to be provided by the counterication(s).

Particularly preferred cations are $Na^+$, $K^+$, $NH_4^+$, $Ca^{2+}$, $Mg^{2+}$, $Al^{3+}$ and $Zn^{2+}$.

It goes without saying that the various 4-hydroxychalcone derivatives and the salts thereof may in each case be used according to the invention alone or as mixtures.

Use according to the invention is also preferred in which, in addition to a compound of the formula (I), a corresponding salt or a corresponding mixture, a further substance is present for modifying, masking or reducing the unpleasant taste impression of an unpleasant tasting substance. A combination of at least two taste-correcting agents is then present.

The known neohesperidin dihydrochalcone displays a bitterness-reducing effect, which is attributable above all, however, to its property as a very strong sweetener (cf. *Manufacturing Chemist* 2000, July issue, pp. 16-17), and also has a troublesome effect in non-sweet applications. From our own investigations it is clear, however, that the 4-hydroxydihydrochalcone derivatives to be used according to the invention of the formula (I) or the salts thereof, such as for example phloretin (compound 4), have only very weak inherent sweetness compared with typical sweet-tasting substances. According to the invention, the 4-hydroxychalcone derivatives of the formula (I) are not used as sweeteners. In addition, the 4-hydroxychalcone derivatives of the formula (I) have further weak intrinsic flavor characteristics which are not sweet (cf. organoleptic profile description in Examples 1-4). No bitterness-masking effect of the at most slightly sweet 4-hydroxychalcone derivatives of the formula (I) or the salts thereof has been described before.

With regard to the occurrence and synthesis of the 4-hydroxychalcone derivatives of the formula (I) used according to the invention, reference is made to U.S. 60/784,444 (now WO 2007/107596). This document as a priority document for WO 2007/014879 is accessible by file inspection and is here referred to in its entirety for the purpose of full disclosure of the present invention.

It has surprisingly been found that the 4-hydroxychalcone derivatives of the formula (I) used according to the invention, even in very low concentrations, may reduce or even completely suppress the unpleasant taste impression, in particular the bitter taste impression, of a high number of substances, in particular of caffeine, theobromine and theophylline, quinine, salicin, arbutin, neohesperidin, naringin, quercitrin, rutin, phloridzin, gallic or ellagic acid esters of carbohydrates (e.g. pentagalloylglucose), optionally galloylated catechols or epicatechols, proanthyocyanidines or procyanidines, thearubigin, quercetin, taxifolin, myricetin, γ-oryzanol, caffeic acid or esters thereof (e.g. chlorogenic acid and isomers), limonoids such as limonin or nomilin from citrus fruits, lupolones and humulones from hops, absinthin from wormwood, amarogentin from gentian, metal salts (in particular potassium, magnesium and calcium salts, potassium chloride, potassium gluconate, potassium carbonate, potassium sulfate, potassium lactate, potassium glutamate, potassium succinate, potassium malate, sodium sulfate, magnesium sulfate) and pharmaceutical active ingredients (e.g. fluoroquinolone antibiotics, paracetamol, aspirin, β-lactam antibiotics, ambroxol, propylthiouracil [PROP], guaifenesin), it being particularly advantageous for the 4-hydroxychalcone derivatives used according to the invention to have virtually no intrinsic flavor and to have no negative influence on the other, as a rule not unpleasant flavor qualities, and in particular even to have a positive influence on the sweet taste of sweet substances.

Surprisingly, it has further been found that the 4-hydroxychalcone derivatives of the formula (I) used according to the invention particularly effectively reduce the bitter taste, above all of potassium salts (in particular potassium chloride, potassium gluconate, potassium carbonate, potassium sulfate, potassium lactate, potassium glutamate, potassium succinate or potassium malate), especially of potassium chloride, in combination with one or more lactones, preferably lactones with a 5- or 6-membered ring, particularly preferably in combination with nonenolide and/or 4-methyl-5-hydroxy-hexanoic acid lactone (4-methyl-delta-hexylactone). In this case, the bitter taste impression of the potassium salts is actually reduced and not for instance overlaid with another, stronger (e.g. sweet) taste impression.

Nonenolide may preferably be used as the (R)- or (S)-enantiomer or in racemic form. 4-Methyl-5-hydroxy-hexanoic acid lactone may be syn- or anti-configured, or be present as an (R,R)-configured enantiomer, (R,S)-configured enantiomer, (S,R)-configured enantiomer, (S,S)-configured enantiomer or as any desired mixture of the enantiomers, in particular as a racemate, or indeed as any desired mixture of the corresponding diastereomers.

As already mentioned, one aspect of the present invention relates to use of a 4-hydroxychalcone derivative of the formula (I) or of a corresponding salt or mixture for masking or reducing the unpleasant taste impression of an unpleasant tasting substance, i.e. as taste-correcting agent. Preferably, the 4-hydroxychalcone derivative of the formula (I) to be used according to the invention, the salt or the mixture are used in a pharmaceutical preparation customized to be taken orally or a preparation serving for nutrition, oral care or pleasure, the preparation conventionally comprising one or more unpleasant tasting substances.

Insofar as the present invention relates to preparations, those preparations which contain phloretin and a) hesperetin and/or b) phloridzin, or another phloretin glycoside, are preferably excepted. Excepted preparations are therefore preferably those which naturally contain the 4-hydroxychalcone derivatives according to the invention of the formula (I) and to which the 4-hydroxychalcone derivatives of the formula (I) are not added from other sources (synthetic or isolated from natural sources) above and beyond the natural quantity. These include in particular many apple-containing preparations (*Malus* ssp.).

If the preparation according to the invention has one or more sweet substances, it is likewise preferred for the sweetness of the preparation according to the invention to have at most 1% sucrose equivalents. Such a preparation according to the invention then has a sweetness which is no greater than that of a 1% sucrose solution. Such solutions are conventionally experienced as not tasting even slightly sweet. In the case of these preparations in particular, the reduction, modification or masking of an unpleasant, in particular a bitter, taste of an unpleasant tasting substance is clearly not attributable to covering the unpleasant taste with the very strong sweetness of the preparation.

Preparations according to the invention preferably comprise 0.000001 wt. % to 95 wt. %, relative to the total weight of the preparation, of a compound to be used according to the invention of the formula (I) (see above), a corresponding salt or mixture. In addition, one or more unpleasant tasting substances are usually present.

Particularly preferred preparations according to the invention are those which comprise at least one unpleasant tasting substance, the amount of the unpleasant tasting substance being sufficient to be perceived as an unpleasant taste in a comparison preparation which does not comprise any 4-hydroxychalcone derivative of the formula (I), salt or mixture of such a 4-hydroxychalcone derivative but which is otherwise of identical composition, and the quantity of the 4-hydroxychalcone derivative of the formula (I), salt or mixture of such a 4-hydroxychalcone derivative in the preparation is sufficient to organoleptically modify, mask or reduce the unpleasant taste impression of the unpleasant tasting substance as compared with the comparison preparation.

Preparations according to the invention may take the form of a semifinished product, an odoriferous, aroma or flavoring substance composition or a seasoning mixture.

Preparations serving for nutrition or for pleasure for the purposes of the invention are for example bakery products (for example bread, dry biscuits, cakes, other pastry products), confectionery (for example chocolates, chocolate bar products, other bar products, fruit gums, hard and soft caramels, chewing gum), alcoholic or non-alcoholic beverages (for example coffee, tea, wine, beverages containing wine, beer, beverages containing beer, liqueurs, spirits, brandies, fruit-containing carbonated beverages, isotonic beverages, soft drinks, nectars, fruit and vegetable juices, fruit or vegetable juice preparations), instant beverages (for example instant cocoa beverages, instant tea beverages, instant coffee beverages), meat products (for example ham, fresh or cured sausage preparations, spiced or marinated fresh or cured meat products), eggs or egg products (dried egg, egg white, egg yolk), cereal products (for example breakfast cereals, muesli bars, precooked ready rice products), dairy products (for example milk beverages, milk ice cream, yoghurt, kefir, curd cheese, soft cheese, hard cheese, dried milk powder, whey, butter, buttermilk, partially or fully hydrolyzed milk protein-containing products), products made from soy protein or other soybean fractions (for example soy milk and products made therefrom, soy lecithin-containing preparations, fermented products such as tofu or tempe or products made therefrom), fruit preparations (for example jams, fruit ice cream, fruit sauces, fruit fillings), vegetable preparations (for example ketchup, sauces, dried vegetables, deep-frozen vegetables, precooked vegetables, preserved vegetables), snack articles (for example baked or fried potato chips or potato dough products, maize- or peanut-based extrudates), fat- or oil-based products or emulsions thereof (for example mayonnaise, remoulade, dressings), other ready-to-serve meals and soups (for example dried soups, instant soups, precooked soups), spices, seasoning mixtures and in particular powdered seasonings, which are for example used in snack food applications. The preparations for the purposes of the invention may also be used as semifinished products for the production of further preparations serving for nutrition or for pleasure. The preparations for the purposes of the invention may also be nutritional supplements in the form of capsules, tablets (uncoated and coated tablets, for example coatings resistant to gastric juices), sugar-coated tablets, granules, pellets, mixtures of solids, dispersions in liquid phases, as emulsions, as powders, as solutions, as pastes or as other swallowable or chewable preparations.

Preparations according to the invention serving for oral care are in particular oral and/or dental care products such as toothpastes, tooth gels, tooth powders, mouthwashes, chewing gum and other oral care products.

Further conventional active ingredients, basic materials, auxiliary substances and additives for preparations serving for nutrition, for oral care or for pleasure or used may be present in quantities of 5 to 99.999999 wt. %, preferably of 10 to 80 wt. %, relative to the total weight of the preparation. The preparations may furthermore comprise water in a quantity of up to 99.999999 wt. %, preferably of 5 to 80 wt. %, relative to the total weight of the preparation.

The preparations according to the invention, containing one or more of 4-hydroxychalcone derivatives used according to the invention of the formula (I) or the salts thereof or mixtures, produced according to a preferred development by incorporating the 4-hydroxychalcone derivatives of the formula (I) or the salts thereof or mixtures as the substances themselves, as a solution or in the form of a mixture with a solid or liquid carrier in an oral pharmaceutical base-preparation or a base preparation serving for nutrition, oral care or pleasure. Preparations according to the invention in the form of a solution may advantageously also be converted into a solid preparation by spray drying.

According to a further preferred embodiment, preparations according to the invention may be produced by incorporating the 4-hydroxychalcone derivative(s) used according to the invention of the formula (I) or the salts or mixtures thereof and optionally other constituents of the preparation according to the invention into emulsions, into liposomes, for example starting from phosphatidyl choline, into microspheres, into nanospheres or also into capsules, granules or extrudates prepared from a matrix suitable for foodstuffs and products consumed for pleasure, for example prepared from starch, starch derivatives, cellulose or cellulose derivatives (for example hydroxypropylcellulose), other polysaccharides (for example alginate), natural fats, natural waxes (for example beeswax, carnauba wax) or from proteins, for example gelatin.

In a further preferred production method, the 4-hydroxychalcone derivatives of the formula (I) or the salts or mixtures thereof are previously complexed with one or more suitable complexing agents, for example with cycloglycans, for example cyclofructans, cyclodextrins or cyclodextrin derivatives, preferably α-, γ- and β-cyclodextrin, and used in this complexed form.

One preparation which is particularly preferred according to the invention is one in which the matrix is so selected that the 4-hydroxychalcone derivatives of the formula (I) are released by the matrix in delayed manner, such that a longlasting action is obtained.

The further constituents for preparations according to the invention may comprise conventional basic materials, auxiliary substances and additives for foodstuffs or products consumed for pleasure. Some of these substances have an unpleasant taste in the sense of the definition given above.

Examples of conventional basic materials, auxiliary substances and additives for foodstuffs or products consumed for pleasure are water, mixtures of fresh or processed, plant or animal basic or raw materials (for example raw, roasted, dried, fermented, smoked and/or boiled meat, bone, cartilage, fish, vegetables, fruit, herbs, nuts, vegetable or fruit juices or pastes or mixtures thereof), digestible or non-digestible carbohydrates (for example sucrose, maltose, fructose, glucose, dextrins, amylose, amylopectin, inulin, xylans, cellulose), sugar alcohols (for example sorbitol), natural or hardened fats (for example tallow, lard, palm fat, coconut oil, hardened vegetable fat), oils (for example sunflower oil, peanut oil, maize germ oil, olive oil, fish oil, soya oil, sesame oil), fatty acids or the salts thereof (for example potassium stearate), proteinogenic or non-proteinogenic amino acids and related compounds (for example taurine), peptides, native or processed proteins (for example gelatin), enzymes (for example peptidases), nucleic acids, nucleotides, taste-correcting agents for unpleasant taste impressions other than those used according to the invention (4-hydroxychalcone derivatives of the formula (I) and lactones as described above), taste-correcting agents for further generally not unpleasant taste impressions, flavor-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols), stabilizers (for example carrageenan, alginate), preservatives (for example benzoic acid, sorbic acid), antioxidants (for example tocopherol, ascorbic acid), chelating agents (for example citric acid), organic or inorganic acidulants (for example malic acid, acetic acid, citric acid, tartaric acid, phosphoric acid), additional bitter substances (for example quinine, caffeine, limonin, amarogentin, humolone, lupolone, catechins, tannins), sweeteners (for example saccharin, cyclamate, aspartame, neotame), mineral salts (for example sodium chloride, potassium chloride, magnesium chloride, sodium phosphates), substances preventing enzymatic browning (for example sulfite, ascorbic acid), essential oils, plant extracts, natural or synthetic dyes or coloring pigments (for example carotenoids, flavonoids, anthocyans, chlorophyll and the derivatives thereof), spices, trigeminally active substances (i.e. substances which are hot, pungent, tingly, rough, astringent or cause hot or cold effects) or plant extracts containing such trigeminally active substances, synthetic, natural or nature-identical aroma substances or odoriferous substances and odor-correcting agents.

Dental care products (as the basis for preparations serving for oral care) which contain the 4-hydroxychalcone derivatives to be used according to the invention of the formula (I), the salts or mixtures thereof generally comprise an abrasive system (abrasive or polishing agent), such as for example silicas, calcium carbonates, calcium phosphates, aluminum oxides and/or hydroxyapatites, surface-active substances such as for example sodium lauryl sulfate, sodium lauryl sarcosinate and/or cocamidopropyl betaine, humectants such as for example glycerol and/or sorbitol, thickeners, such as for example carboxymethylcellulose, polyethylene glycols, carrageenan and/or Laponite®, sweeteners, such as for example saccharin, other taste-correcting agents for unpleasant taste impressions, taste-correcting agents for further generally not unpleasant taste impressions, flavor-modulating substances (for example inositol phosphate, nucleotides such as guanosine monophosphate, adenosine monophosphate or other substances such as sodium glutamate or 2-phenoxypropionic acid), cooling active ingredients such as for example menthol, menthol derivatives (for example L-menthol, L-menthyl lactate, L-menthyl alkylcarbonates, menthone ketals, menthane carboxamides), 2,2,2-trialkylacetamides (for example 2,2-diisopropyl propionic acid methylamide), icilin derivatives, stabilizers and active ingredients, such as for example sodium fluoride, sodium monofluorophosphate, tin difluoride, quaternary ammonium fluorides, zinc citrate, zinc sulfate, tin pyrophosphate, tin dichloride, mixtures of different pyrophosphates, triclosan, cetylpyridinium chloride, aluminum lactate, potassium citrate, potassium nitrate, potassium chloride, strontium chloride, hydrogen peroxide, aromas and/or sodium bicarbonate or odor-correcting agents).

Chewing gums (as a further example of the preparations serving for oral care) which contain 4-hydroxychalcone derivatives to be used according to the invention generally comprise a chewing gum base, i.e. a chewable mass which becomes plastic on chewing, sugars of various kinds, sugar substitutes, sweeteners, sugar alcohols, other taste-correcting agents for unpleasant taste impressions, taste-correcting agents for further, generally not unpleasant taste impressions, flavor-modulating substances (for example inositol phosphate, nucleotides such as guanosine monophosphate, adenosine monophosphate or other substances such as sodium glutamate or 2-phenoxypropionic acid), the cooling active ingredients, humectants, thickeners, emulsifiers, aromas and stabilizers or flavor-correcting agents mentioned in the above paragraph.

Preferably, the preparations according to the invention may also contain an aroma composition in order to round off and refine the flavor and/or odor of the preparation. Suitable aroma compositions contain for example synthetic, natural or nature-identical aroma, odoriferous and flavor substances and suitable auxiliary substances and carriers.

Preparations according to the invention which serve as semifinished products generally contain 0.0001 wt. % to 95 wt. %, preferably 0.001 to 80 wt. %, but in particular 0.01 wt. % to 50 wt. %, relative to the total weight of the preparation, of 4-hydroxychalcone derivatives to be used according to the invention of the formula (I), the salts thereof or mixtures thereof. Preparations according to the invention which are present as semifinished products may serve to mask or reduce the unpleasant taste impression of finished product preparations which are produced using the semifinished product preparation.

In a particularly preferred embodiment of the invention, the 4-hydroxychalcone derivatives according to the invention of the formula (I), the salts or mixtures thereof are used in the preparations according to the invention in combination with at least one further (other) substance to modify, mask or reduce the unpleasant taste impression of an unpleasant tasting substance. In this way, particularly active masking may be achieved.

The further taste-correcting agents may be selected from the following list, without the invention being limited thereto: nucleotides (for example adenosine 5'-monophosphate, cytidine 5'-monophosphate, inosine 5'-monophosphate) or the pharmaceutically acceptable salts thereof, lactisole, 2,4-dihydroxybenzoic acid, 3-hydroxybenzoic acid, sodium salts (for example sodium chloride, sodium lactate, sodium citrate, sodium acetate, sodium gluconate), hydroxyflavanones (for example eriodictyol, homoeriodictyol or the sodium salts thereof, in particular according to EP 1 258 200, hydroxybenzoic acid amide (for example 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxy-benzyl)amide, 2-hydroxybenzoic acid N-(4-hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-2-(4-hydroxy-3-methoxyphenyl)ethylamide, 2,4-dihydroxybenzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), hydroxydeoxybenzoins (for example 2-(4-hydroxy-3-methoxyphenyl)-1-(2,4,6-trihydroxyphenyl)ethanone, 1-(2,4-dihydroxyphenyl)-2-(4-hydroxy-3-methoxy-phenyl)ethanone, 1-(2-hydroxy-4-methoxyphenyl)-2-(4-hydroxy-3-methoxyphenyl)ethanone, hesperetin according to WO 2007/014879, diacetyl trimers according to WO 2006/058893, deoxybenzoins according to WO 2006/106023, ginger diones according to WO 2007/003527, mixtures for amplifying salty taste according to PCT/EP 2006/067120 and documents based thereon, amino acids (for example gamma aminobutyric acid, taurine, beta-alanine, arginine, ornithine, lysine), divanillin according to WO 2004/078302, pellitorines according to WO 2004/043960 and WO 2004/000787, lactones as mentioned above, preferably nonenolide and/or 4-methyl-5-hydroxy-hexanoic acid lactone or mixtures thereof, or mixtures of whey proteins with lecithins.

Particularly preferred taste-correcting agents are 2,4-dihydroxybenzoic acid, 3-hydroxybenzoic acid, sodium lactate, sodium citrate, sodium acetate, sodium gluconate, hydroxyflavanones (for example eriodictyol, homoeriodictyol or the sodium salts thereof), in particular according to EP 1 258 200, hydroxybenzoic acid amide (for example 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid N-(4-hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxy-benzyl)amide monosodium salt, 2,4-dihydroxybenzoic acid N-2-(4-hydroxy-3-methoxyphenyl)ethylamide, 2,4-dihydroxybenzoic acid N-(4-hydroxy-3-ethoxy-benzyl)amide, 2,4-dihydroxybenzoic acid N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), hydroxydeoxybenzoins (for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone, hesperetin according to WO 2007/014879, diacetyl trimers according to WO 2006/058893, deoxybenzoins according to WO 2006/106023, ginger diones according to WO 2007/003527, divanillin according to WO 2004/078302, pellitorines according to WO 2004/043960 and WO 2004/000787, lactones as mentioned above, preferably nonenolide and/or 4-methyl-5-hydroxy-hexanoic acid lactone or mixtures thereof.

Particularly preferred are hydroxy flavanones (for example eriodictyol, homoeriodictyol or the sodium salts thereof), in particular according to EP 1 258 200, 2,4-dihydroxybenzoic acid vanillylamide, 2,4,6-trihydroxybenzoic acid N-(4-hydroxy-3-methoxybenzyl)amide, 2,4-dihydroxybenzoic acid N-(4-hydroxy-3-methoxybenzyl)amide monosodium salt, hesperetin according to WO 2007/014879, diacetyl trimers according to WO 2006/058893, ginger dione [2] according to WO 2007/003527, divanillin according to WO 2004/078302, trans-pellitorine according to WO 2004/043960 and WO 2004/000787, lactones as mentioned above, preferably nonenolide and/or 4-methyl-5-hydroxy-hexanoic acid lactone or mixtures thereof.

In a further, particularly preferred embodiment of the invention, the 4-hydroxychalcone derivatives according to the invention of the formula (I), the salts or mixtures thereof, optionally together with the above-stated further taste-correcting agents, are used in combination with one or more substances which have an unpleasant aftertaste with a not unpleasant primary flavor (for example sweet, salty, spicy, sour), preparations according to the invention being obtained which may also serve to produce ready-to-eat preparations in which the unpleasant aftertaste of the unpleasant tasting substances is then masked or reduced. In these preparations, substances used which have an unpleasant aftertaste with a not unpleasant primary flavor are above all potassium salts (in particular potassium chloride, potassium gluconate, potassium carbonate, potassium sulfate, potassium lactate, potassium glutamate, potassium succinate or potassium malate), aspartame, neotame, superaspartame, saccharin, sucralose, tagatose, monellin, stevioside, rebaudioside, hernandulcin, thaumatin, miraculin, glycyrrhizin, glycyrrhetinic acid or derivatives thereof, cyclamate or the pharmaceutically acceptable salts of the above-mentioned compounds.

EXAMPLES

The examples serve to clarify the invention, without limiting the scope of protection of the claims.

Example 1

Phloretin, Compound 4

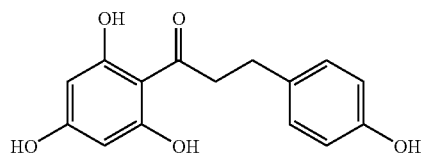 [SMILES: O=C(CCc1ccc(O)cc1)c1c(O)cc(O)cc1O]

Commercial phloretin (Sigma-Aldrich, order no. P 7912, CA no. 60-82-2, purity >98%) was used.

Organoleptic profile in 5 wt. % aqueous sugar solution (sucrose):
sweet, astringent, dusty-dry Example 2

Compound 6, 2',4,4'-trihydroxy-3-methoxydihydrochalcone

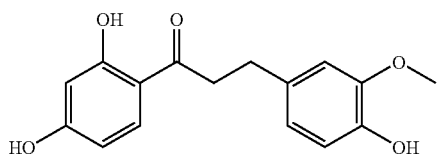 [SMILES: COc1cc(CCC(=O)c2ccc(O)cc2O)ccc1O]

Synthesis was described in U.S. 60/784,444, Example 3.
Organoleptic profile in 5 wt. % aqueous sugar solution (sucrose):
relatively neutral, slight syrupy note Example 3

Compound 10,
4,4'-dihydroxy-3-methoxydihydrochalcone

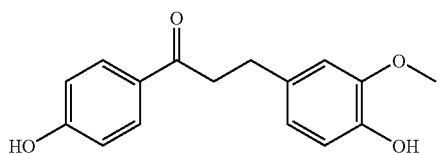 [SMILES: COc1cc(CCC(=O)c2ccc(O)cc2)ccc1O]

Synthesis proceeded in a manner similar to that described in U.S. 60/784,444, Example 3.

Organoleptic profile in 5 wt. % aqueous sugar solution (sucrose):

neutral

Example of Application 1

Reducing Bitterness of a Bitter Substance Solution

In order to quantify the reduction in the bitter impression, the bitterness of an aqueous bitter substance solution and a sample containing the same quantity of bitter substance and a varying quantity of the exemplary compound, was determined by a panel of experts (rating 0 [not bitter] to 10 [extremely bitter]). Evaluation took place by calculating the reduction (in %) in the bitter impression from the average values of the assessments of the bitter substance solution or the solutions containing bitter substance and exemplary compound. 274-Dihydroxybenzoic acid (2,4-DHB) was used as a comparison from U.S. Pat. No. 5,643,941.

TABLE

Bitterness of a bitter substance solution and of a solution containing bitter substance and an exemplary compound (2,4-DHB = 2,4-dihydroxybenzoic acid).

| Substance | Bitter substance | Tester Total | Tester positive | Bitter impression (1-10) without | Bitter impression (1-10) with | % reduction in bitter impression |
|---|---|---|---|---|---|---|
| 100 ppm 2,4-DHB | 500 ppm caffeine | 15 | 9 | 5.1 ± 1.0 | 5.0 ± 1.0 | 3%, n.s. |
| 50 ppm Compound 4, phloretin | 500 ppm caffeine | 16 | 13 | 5.5 ± 0.9 | 3.9 ± 1.8 | 28%, $p < 0.05$ |
| 30 ppm Compound 4, phloretin | 5 ppm quinine hydrochloride | 15 | 10 | 3.9 ± 2.2 | 2.0 ± 1.4 | 25%, n.s. |
| 30 ppm Compound 4, phloretin | 250 ppm salicin | 15 | 10 | 7.3 ± 2.0 | 6.0 ± 1.8 | 18%, $p < 0.1$ |
| Compound 6, 2',4,4'-trihydroxy-3-methoxydihydrochalcone | 500 ppm caffeine | 15 | 11 | 4.4 ± 1.1 | 3.3 ± 0.7 | 24%, n.s. |
| 50 ppm Compound 10, 4,4'-dihydroxy-3-methoxydihydrochalcone | 500 ppm caffeine | 15 | 15 | 5.2 ± 0.9 | 3.7 ± 0.8 | 29%, $p < 0.05$ |

TABLE-continued

Bitterness of a bitter substance solution and of a solution containing bitter substance and an exemplary compound (2,4-DHB = 2,4-dihydroxybenzoic acid).

| Substance | Bitter substance | Tester Total | Tester positive | Bitter impression (1-10) without | Bitter impression (1-10) with | % reduction in bitter impression |
|---|---|---|---|---|---|---|
| 50 ppm Compound 10, 4,4'-dihydroxy-3-methoxy-dihydrochalcone | 5 ppm quinine hydrochloride | 13 | 11 | 3.6 ± 1.0 | 2.4 ± 0.8 | 34%, p < 0.1 |

"Tester positive" means the number of testers who were able to identify masking;
the 95% confidence ranges are stated as errors;
p < x means the significance according to Student's t-test method (cf. statistics textbooks),
n.s. means not significant.

Example of Application 2

Reduction in Unpleasant Taste Impressions of Potassium Chloride-Containing Preparations A fat- and common salt-free meat stock is prepared with 0.4 wt. % sodium chloride and 0.4 wt. % potassium chloride (in each case relative to total weight) (comparison solution A). The same solution is prepared again and a quantity of phloretin (compound 4 from Example 1) is added. Solution A is served up to the testers once with the designation "standard solution", and at the same time solution A and solution B are served up as "test solution 1" or "test solution 2" in a random order unknown to the respective tester (i.e. solutions A and B may have different designations for different testers; each tester has to test three solutions). In a first test phase, the testers are asked whether one of the three solutions tastes different from the other two (triangle difference testing). If the response to this question is "No", the test is stopped for that tester. If the response to this question is "Yes", the tester has to quantify the flavor qualities, listed below, of "test solution 1" or "test solution 2" deviating from the "standard solution" (relative to the "standard solution", 0 flavor quality identical to the standard, −4 very much weaker than the standard, +4 very much stronger than the standard). Taking as basis the results from all the testers, the average of all deviations from the "standard solution" is calculated for the individual flavor qualities.

Although the exemplary application is somewhat less salty and sweeter than the "standard solution", it displays a significantly less bitter aftertaste and is therefore preferred.

Example of Application 3

Spray-Dried Preparation as Semifinished Product for Aromatization of Finished Products

| Constituent | Quantity used in wt. % |
|---|---|
| Drinking water | 60.8% |
| Maltodextrin from wheat | 24.3% |
| Gum arabic | 6.1% |
| Phloretin (compound 4 from Example 1) | 8.8% |

The drinking water is initially introduced into a container and the maltodextrin and gum arabic are dissolved therein. Then the phloretin (Example 1; compound 4) is emulsified into the carrier solution with a Turrax. The temperature of the spray solution should not exceed 30° C. The mixture is then spray-dried (specified inlet temperature: 185-195° C., specified outlet temperature: 70-75° C.). The spray-dried semifinished product contains approx. 18-22% of the active ingredient from Example 2.

| Substance | Salty | Sweet | Sour | Bitter | Mouth fullness | Aromaticity | Number of testers | Positive testers |
|---|---|---|---|---|---|---|---|---|
| Phloretin (compound 4 from Example 1), 30 ppm | −0.7 | 0.9 | 0.1 | −0.4 | 0.3 | −0.1 | 21 | 16 (p < 0.05) |

Spray-dried preparations may likewise be produced as semifinished products from Example 2 (compound 6).

Example of Application 4

Black Tea Preparation

| Constituent | Quantity used in wt. % |
|---|---|
| Black tea, Ceylon, leaf | 94.00% |
| Semifinished product from Example of application 2, containing approx. 18-22% phloretin (compound 4 from Example 1) | 6% |

The tea and the semifinished product are mixed and packaged in teabags of filter paper. For use, 100-250 ml of boiling water are poured onto the teabag, which is left to brew for 2-5 min.

Example of Application 5

Black Tea Preparation in Combination with Homoeriodictyol Sodium Salt

| Constituent | Quantity used in wt. % |
|---|---|
| Black tea, Ceylon, leaf | 94.00% |
| Semifinished product from Example of application 2, containing approx. 18-22% phloretin (compound 4 from Example 1) | 3% |
| Semifinished product made from homoeriodictyol sodium salt according to EP 1258200 B1, spray-dried in a manner similar to Example of application 2 | 3% |

The tea and the semifinished product are mixed and packaged in teabags of filter paper. For use, 100-250 ml of boiling water are poured onto the teabag, which is left to brew for 2-5 min.

Example of Application 6

Use in a Soy Beverage

Phloretin from Example 1 was predissolved in ethanol and added to a soy milk from a local supermarket. The mixture was stirred together with the milk aroma in the beaker.

| Constituent | Quantity used in wt. % |
|---|---|
| Soy milk (local supermarket) | 99.8% |
| Milk aroma | 0.1% |
| 10% Phloretin (compound 4 from Example 1) in ethanol | 0.1% |

Example of Application 7

Use in a Soy Beverage in Combination with γ-Aminobutyric Acid

γ-Aminobutyric acid was predissolved in water and phloretin (compound 4, Example 1) in ethanol and added to a soy milk from a local supermarket. The mixture was stirred together with the milk aroma in the beaker.

| Constituent | Quantity used in wt. % |
|---|---|
| Soy milk (local supermarket) | 99.7% |
| Milk aroma | 0.1% |
| 10% Phloretin (compound 4 from Example 1) in ethanol | 0.1% |
| 1% γ-aminobutyric acid in water | 0.1% |

Example of Application 8

Use in a Bitter Chocolate

The spray-dried preparation from Example of application 2 was incorporated into the chocolate melted at 40° C. and the liquid mass was cast into a slab mold and cooled using the tempering method known to a person skilled in the art, eating chocolate being obtained.

| Constituent | Quantity used in wt. % |
|---|---|
| Bitter chocolate, min. 85% cocoa (commercial product) | 99.8% |
| Spray-dried preparation from Example of application 2 | 0.2% |

The trained specialists found the chocolate prepared in this way to be less bitter, less astringent and altogether more rounded.

Example of Application 9

Aroma for Reducing the Bitter Taste Quality of Potassium Salt-Containing Preparations

| | Quantity used in wt. % | | | |
|---|---|---|---|---|
| Constituent | Preparation A | Preparation B | Preparation C | Preparation D |
| Phloretin (compound 4 from Example 1) | 1% | 1% | 1% | 1% |
| Hesperetin, spray-dried | | 9% | | |
| Trans-pellitorine according to WO 2004/043960, spray-dried | 16.5% | 16.5% | | |
| Divanillin, spray-dried | 5% | 5% | 5% | 5% |
| Maltodextrin | 68.5% | 65.7% | 94.7% | 93.7% |
| Nonenolide | | | | 0.3% |
| 4-Methyl-5-hydroxy-hexanoic acid lactone | | | 0.3% | |

Example of Application 10

Masking of Potassium Salt-Containing Spreads

Potassium chloride (4%) was introduced in the aqueous phase into a commercially available medium-fat margarine (40% fat) (standard preparation). After dividing up the mass, the preparation D according to Example of application 9 was introduced into one half and rehomogenized (test preparation). The standard preparation was compared organoleptically with the test preparation: the standard preparation is distinctly saltier and more bitter, in particular in aftertaste, than the test preparation. The test preparation was preferred by most testers.

Example of Application 11

Improvement of Green Tea Preparations

Preparation A: comparison preparation without masking
Preparation B and C: preparations according to the invention

| | Quantity used in wt. % | | |
|---|---|---|---|
| Constituent | Preparation A | Preparation B | Preparation C |
| Sucrose | 5% | 5% | 5% |
| Green tea extract (aqueous, spray-dried) | 0.33% | 0.33% | 0.33% |
| Phloretin (compound 4 from Example 1) | — | 0.005% (=50 ppm) | — |
| 4,4'-Dihydroxy-3-methoxydihydrochalcone (compound 10 from Example 3) | — | — | 0.005% (=50 ppm) |
| Water | to make up to 100% | to make up to 100% | to make up to 100% |

The ingredients were mixed in the stated order and then assessed as follows by a panel (15 testers), each tester was given 3 test samples, of which one was sample A (comparison sample, made known to the tester), another was sample A (this time not known to the tester) and the final sample was sample B (not known to the tester). The latter two samples were presented to the testers in randomized order. In the first test phase the examiners had to decide whether they could distinguish one of the latter two samples from the comparison sample. If yes, the testers had to decide using a scale running from −4 (much weaker), −3, −2, −1, 0 (no difference), 1, 2, 3, 4 (much stronger) to what extent the astringency, bitterness and sweetness (in each case individually assessed) differ from the known comparison sample.

The test was performed again identically, except that preparation C was tested instead of B.

The results are presented in the following Table:

| Preparation | Bitterness - deviation from Preparation A | Astringency - deviation from Preparation A | Sweetness - deviation from Preparation A | Significant difference ($p < 0.05$)? |
|---|---|---|---|---|
| B | −0.20 | 0.27 | 0.53 | yes |
| C | −0.27 | 0.20 | −0.47 | yes |

In preparation B, bitterness was reduced relative to comparison preparation A, while astringency was increased slightly, and in particular also sweetness. In preparation C, bitterness was reduced markedly relative to comparison preparation A, astringency increased a little and sweetness somewhat reduced.

Further Examples of application are described in U.S. 60/784,444.

The invention claimed is:

1. A preparation, comprising:
   a) one or more 4-hydroxychalcone derivatives selected from the group consisting of:
      3-(4-hydroxyphenyl)-1-(2,4,6-trihydroxyphenyl)propan-1-one (phloretin), and/or a salt thereof,
      3-(4-hydroxy-3-methoxyphenyl)-1-(2,4-dihydroxyphenyl)propan-1-one, and/or a salt thereof, and
      3-(4-hydroxy-3-methoxyphenyl)-1-(4-hydroxyphenyl)propan-1-one, and/or a salt thereof; and
   b) one or more unpleasant tasting substances;
   provided that
      i) the 4-hydroxychalcone derivative is not 3-(4-hydroxyphenyl)-1-(2,4,6-trihydroxyphenyl)propan-1-one (phloretin) if the preparation contains hesperetin, phloridzin, or another phloretin glycoside, or
      ii) if the preparation contains one or more sweet-tasting substances, the sweetness of the preparation amounts to at most 1% sucrose equivalents.

2. The preparation as claimed in claim 1, wherein the unpleasant tasting substance(s) is or are selected from the group consisting of: xanthine alkaloids; xanthines; alkaloids; phenolic glycosides; flavonoid glycosides; bitter tasting chalcones or chalcone glycosides; non-hydrolyzable tannins; flavones; phenols; polyphenols; terpenoid bitter substances; absinthin; amarogentin; metal salts; pharmaceutical active ingredients; vitamins; denatonium benzoate; sucralose octaacetate; iron salts; aluminum salts; zinc salts; urea; unsaturated fatty acids; bitter tasting amino acids; and bitter tasting peptides.

3. The preparation as claimed in claim 1, wherein the preparation is an oral pharmaceutical preparation, a preparation serving for nutrition, a preparation serving for pleasure or a preparation serving for oral hygiene.

4. The preparation as claimed in claim 1, wherein the preparation, relative to its total weight, contains a total of 0.000001 to 95 wt. % of the one or more 4-hydroxychalcone derivative(s), and/or salt(s) thereof.

5. The preparation as claimed in claim 1, wherein the preparation is in the form of a semifinished product, an odoriferous, aroma or flavoring substance composition, or a seasoning mixture.

6. The preparation as claimed in claim 1, further comprising at least one further substance for modifying, masking or reducing the unpleasant taste impression of an unpleasant tasting substance.

7. A method for masking or reducing the unpleasant taste impression of an unpleasant tasting substance in a preparation comprising mixing one or more unpleasant tasting substances with one or more 4-hydroxychalcone derivatives selected from the group consisting of:
   3-(4-hydroxyphenyl)-1-(2,4,6-trihydroxyphenyl)propan-1-one (phloretin), and/or a salt thereof,
   3-(4-hydroxy-3-methoxyphenyl)-1-(2,4-dihydroxyphenyl)propan-1-one, and/or a salt thereof, and
   3-(4-hydroxy-3-methoxyphenyl)-1-(4-hydroxyphenyl)propan-1-one, and/or a salt thereof;
   provided that
   i) the 4-hydroxychalcone derivative is not 3-(4-hydroxyphenyl)-1-(2,4,6-trihydroxyphenyl)propan-1-one if the preparation contains hesperetin, phloridzin, or another phloretin glycoside, or
   ii) if the preparation contains one or more sweet-tasting substances, the sweetness of the preparation amounts to at most 1% sucrose equivalents.

8. The method of claim 7, additionally comprising mixing the one or more hydroxychalcone derivatives and one or more unpleasant tasting substances with at least one lactone.

9. The method of claim 8, wherein the at least on lactone is nonenolide and/or 4-methyl-5-hydroxyhexanoic acid lactone.

10. The method of claim 4, wherein the unpleasant tasting substance is a bitter tasting substance.

11. The method of claim 10, wherein the bitter tasting substance is a potassium salt.

12. The method of claim 11, wherein the potassium salt is potassium chloride.

13. The method of claim 7, additionally comprising mixing the one or more hydroxychalcone derivatives and the one or more unpleasant tasting substances with eriodictyol, homoeriodictyol and/or a sodium salt thereof.

* * * * *